United States Patent [19]

Wylie et al.

[11] Patent Number: 5,939,612
[45] Date of Patent: Aug. 17, 1999

[54] RETENTION TIME-LOCKED SPECTRAL DATABASE FOR TARGET ANALYTE ANALYSIS

[75] Inventors: Philip L. Wylie, Kennett Square, Pa.; James H. Crabtree, Long Beach, Calif.; Kenneth R. Weiner, Yardley, Pa.

[73] Assignee: Hewlett-Packard Company, Palo Alto, Calif.

[21] Appl. No.: 09/067,517

[22] Filed: Apr. 28, 1998

[51] Int. Cl.[6] .......................... B01D 15/08; G01N 30/02; G06F 15/20
[52] U.S. Cl. ...................... 73/23.36; 73/23.35; 73/61.52; 422/89; 422/68.1; 95/82; 210/656; 436/161
[58] Field of Search ............................... 73/61.52, 23.35, 73/23.41, 23.36, 61.57, 23.37; 210/565; 95/82; 422/89, 68.1; 436/161

[56] References Cited

U.S. PATENT DOCUMENTS

| | | | |
|---|---|---|---|
| 3,717,028 | 2/1973 | Annino et al. | 73/23.1 |
| 3,898,837 | 8/1975 | Boege | 73/23.1 |
| 4,181,613 | 1/1980 | Welsh et al. | 210/179 |
| 4,353,242 | 10/1982 | Harris et al. | 73/23.1 |
| 4,740,903 | 4/1988 | Nakatsuka et al. | 364/497 |
| 4,807,148 | 2/1989 | Lacey | 364/498 |
| 4,824,446 | 4/1989 | Mowery, Jr. | 55/67 |
| 4,835,708 | 5/1989 | Frans | 364/497 |
| 4,927,532 | 5/1990 | Pospisil et al. | 210/198.2 |
| 4,994,096 | 2/1991 | Klein et al. | 55/20 |
| 5,106,756 | 4/1992 | Zaromb | 436/161 |
| 5,108,468 | 4/1992 | Ligon, Jr. | 55/67 |
| 5,116,764 | 5/1992 | Annino et al. | 436/161 |
| 5,163,979 | 11/1992 | Patrick et al. | 55/21 |
| 5,175,430 | 12/1992 | Enke et al. | 250/282 |
| 5,281,397 | 1/1994 | Ligon et al. | 422/89 |
| 5,339,673 | 8/1994 | Nakagawa et al. | 73/23.36 |
| 5,354,474 | 10/1994 | LaPack et al. | 210/637 |
| 5,398,539 | 3/1995 | Gordon et al. | 73/23.35 |
| 5,405,432 | 4/1995 | Snyder et al. | 95/82 |
| 5,411,707 | 5/1995 | Hiatt | 422/68.1 |
| 5,436,166 | 7/1995 | Ito et al. | 436/161 |
| 5,467,635 | 11/1995 | Nakagawa et al. | 73/23.35 |
| 5,492,555 | 2/1996 | Strunk et al. | 95/86 |
| 5,559,728 | 9/1996 | Kowalski et al. | 364/571.02 |
| 5,592,402 | 1/1997 | Beebe et al. | 364/578 |
| 5,670,379 | 9/1997 | Ito et al. | 436/161 |

OTHER PUBLICATIONS

HP 5898A Microbial Identification System Operating Manual; Version 3.0; pp. 10–13 & 10–14; P/N 19298–90100; Mar., 1984 (Rev. Oct. 1987).

"Standard Test Method for Detailed Analysis Of Petroleum Naphthas Through n–Nonane By Capillary Gas Chromatography;" ASTM Committee D–2 on Petroleum Products and Lubricants; Published Oct., 1992 (Originally published as D 5134–90.

Hewlett–Packard Company Operation Manual; "5880A Gas Chromatograph PNA Analyzer, Option 850," Oct. 1982, Revised Jul. 1983; P/N 18900–90850.

Hewlett–Packard Company Operation Manual "The HP5880A Gas Chromatograph and the HP85 Computer Configured for PNA Analysis," P/N 18900–9063, Mar., 1985; Rev.B, Apr. 1968. Rev C.

*Primary Examiner*—Hezron Williams
*Assistant Examiner*—J. David Wiggins
*Attorney, Agent, or Firm*—Richard F. Schuette

[57] ABSTRACT

Screening an unknown sample for a plurality of known or "target" analytes may be accomplished by creating and searching a retention time-locked spectral database for the entire chromatographic output of a locked GC system locked to such spectral database. Identification of target analytes having for example, known significant mass spectral ions and mass ion ratios corresponding to known analytes of interest believed to be found within a pre-defined retention time window is improved by direct comparison of significant mass spectral ions and the mass ion ratios within a specified retention time window.

14 Claims, 4 Drawing Sheets

RETENTION TIME-LOCKED SPECTRAL DATABASE FOR TARGET ANALYTE ANALYSIS

FIELD OF THE INVENTION

The present invention relates to methods for screening an unknown sample for a plurality of known or "target" analytes and, more particularly, creating and searching a retention time-locked spectral database such that the entire chromatographic output of a locked GC system may be screened for target analytes having for example, known significant mass spectral ions and mass ion ratios corresponding to known analytes of interest believed to be found within a pre-defined retention time window.

BACKGROUND OF THE INVENTION

Gas chromatography is based on the premise that the combination of analytes making up a sample introduced into a column within a gas chromatograph separate as they flow through the column at different rates and subsequently exit the column after different retention times.

In GC/MS analyses today, it is typical to analyze an unknown sample in a scanning mode, and then attempt to identify the resulting chromatographic peaks by mass spectral library searching. Such searching attempts to match a spectrum of the unknown analyte or combination of analytes to one or more spectra contained in a large mass spectral library. It is normal for software associated with the MS detector to report multiple matches (typically 10–20) with a number from 1 to 99 representing the closeness of the match. Retention time has not been employed as a qualifier for matching the analytes, because variations between the column and operating parameters of the GC system used to form the mass spectral library and those of another GC system employed for identifying analytes of interest resulted in large variations in retention time. In particular, variations may be due to instrument calibration, atmospheric temperature and pressure changes, oven design, column length, diameter, film thickness, phase type, and column degradation. These variations may be compounded over time, as it typically takes from weeks to years to conduct all of the analysis required to complete a detailed mass spectral library. Very often, many analytes are reported with similar match quality numbers because mass spectral library searching alone often cannot identify an analyte unequivocally. A prior art method for locking retention time by calculating an adjustment to the column head pressure required to lock a GC system to another GC system results in the retention time of an analyte of interest on both GC systems being the same is illustrated in FIG. 1. Retention time locking is more fully disclosed in commonly assigned U.S. patent applications Ser. No. 09/036658, filed on Mar. 6, 1998 entitled "Automated Retention Time Locking", Ser. No. 08/728,868, filed on Oct. 10, 1996 entitled "Automated Retention Time Locking", and commonly assigned U.S. patent application Ser. No. 08/846,977, filed on Apr. 30, 1997 entitled "Method for Sample Identification Using a Locked Retention Time Database" all of which are hereby incorporated by reference.

It is usually very tedious and impractical to search an entire chromatogram for analytes of interest in a large list. It would be advantageous if the analyst already knew where each analyte of interest will elute in the chromatogram if present, and extract ions inside a narrow window at that retention time to confirm the presence of the analyte. In this manner, retention time is employed as an orthogonal piece of information used to identify an analyte.

It would be advantageous to develop a retention time locked spectral database based on the results obtained using Mass Spectrometry (MS), Infrared detection (IR), Atomic Emission detection (AED) or other spectral detectors which are indexed by retention time of target analytes, their significant spectral data and ratios. For example, a mass spectral database could provide for identification of target analytes through the matching of significant mass spectral ions and the mass ion ratios with retention times in the retention time-locked spectral database if another GC system having the same column and operational parameters could be locked to the reference GC system. There is a need for a method that can use both retention time and spectral information to identify target analytes of interest.

SUMMARY OF THE INVENTION

The present invention relates to methods for screening an unknown sample for a plurality of known or "target" analytes and, more particularly, creating and searching a retention time-locked spectral database such that the entire chromatographic output of a locked GC system may be screened for target analytes having for example, known significant mass spectral ions and mass ion ratios within pre-defined retention time windows.

The retention time-locked spectral database comprises a plurality of data sets, each data set having a defined retention time window, analyte identity, and spectral data for a corresponding one of the plurality of known analytes. A locked GC system is employed for acquiring retention time and spectral data for an unknown sample. In order to identify the analytes present in the unknown sample, a data set for a first known analyte is selected from the database. In particular, a narrow retention time window is defined around the retention time of the first known analyte and the corresponding spectral data is extracted for the unknown sample that occurred within the retention time window for comparison with the spectral data for the first known analyte to determine whether the first known analyte is present in the unknown sample. The steps of selecting, defining, extracting, and comparing for each known analyte in the spectral database are repeated so as to screen the unknown sample for all known analytes.

The retention time-locked spectral database is constructed under locked conditions by adjusting the column head pressure of a reference chromatographic system such that a reference void time, or a reference retention time of a reference analyte, is maintained at a predefined value. A first known analyte is injected into the reference gas chromatographic system and the retention time and spectral data of the first known analyte are measured. A first data set including the retention time, analyte identity, and spectral data of the known analyte is recorded in the spectral database and the steps of injecting, measuring, and recording for each known analyte are repeated so as to construct each data set of the spectral database. Once the spectral database has been created, it can be used to analyze detector scan runs for any compound in the database as long as the same method, nominal column and retention time locking are employed.

The invention provides for the screening of almost any number of unknown samples in a single chromatographic run. New analytes of interest may be searched by adding the corresponding data set of locked retention time, analyte identity and spectral data obtained in a locked GC system. A database comprising more analytes than practical using prior methods can be constructed in this way.

Completely automated analyses may be obtained from the use of the invention, including the use of a centralized database that is accessible from networks by Internet enabled distributed chromatographs or data systems containing spectral data and retention times obtained under locked conditions.

Other aspects and advantages of the present invention will be come apparent from the following detailed description, taken in conjunction with the accompanying drawings, illustrating by way of example the principles of the invention.

DETAILED DESCRIPTION OF THE PREFERRED EMBODIMENTS

Screening an unknown sample for a plurality of known or "target" analytes may be accomplished by creating and searching a retention time-locked spectral database for the entire chromatographic output of a locked GC system. Identification of target analytes having for example, known significant mass spectral ions and mass ion ratios corresponding to known analytes of interest believed to be found within a pre-defined retention time window is improved by direct comparison of significant mass spectral ions and the mass ion ratios within a specified retention time window. In particular, locked retention times provide for narrow retention time windows, and narrow retention time windows provide far fewer analytes that could have the target matching spectral ions and mass ion ratios.

Figure 1:
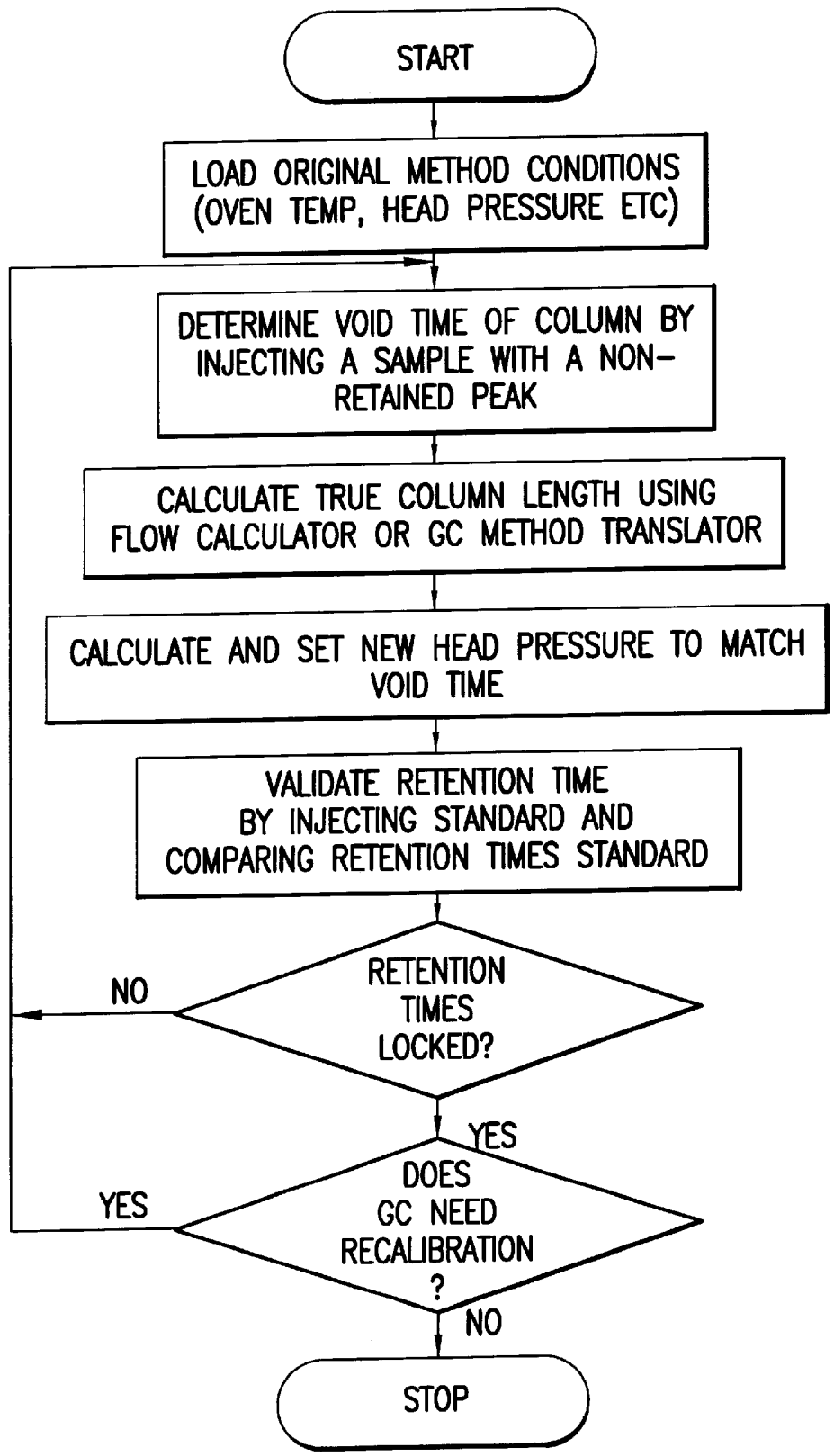
FIG. 1 is a prior art flowchart highlighting method steps for retention time locking through matching of column void times.
Figure 2:
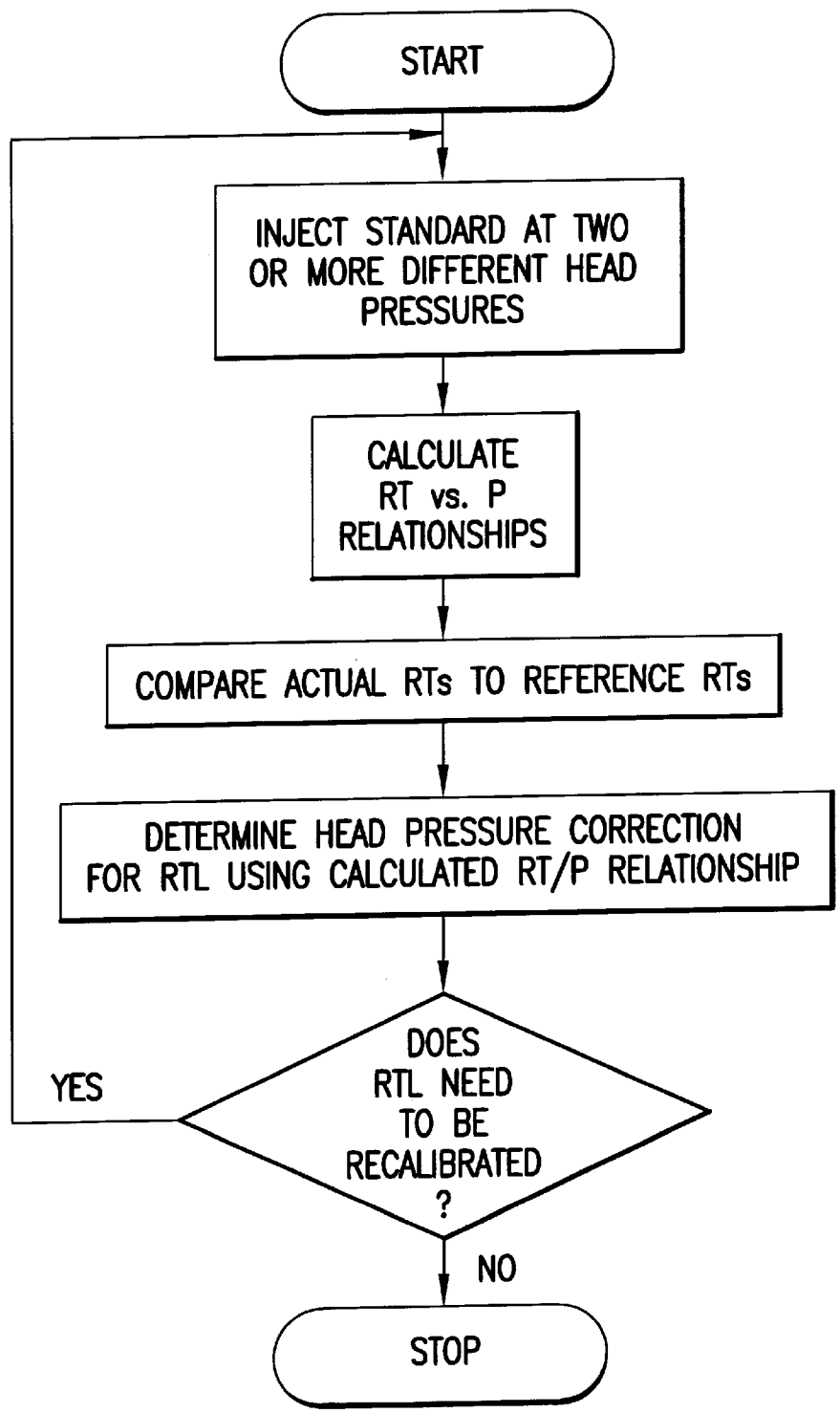
FIG. 2 is a prior art flowchart highlighting the method steps for retention time locking based retention time versus pressure relationships.

Another known method for retention time locking a gas chromatography system is illustrated in FIG. 2, in which a known analyte or "standard" is injected into a reference GC system at a nominal column head pressure to obtain a reference retention time. The standard is further injected into the reference system one or more times at a column head pressure above the nominal pressure, and one or more times at a column head pressure below the nominal pressure. The measured retention times from each injection are used to establish a mathematical relationship between the change in column head pressure and the change in retention time. A target GC system can then be "locked" to the reference GC system by varying the head pressure according to this relationship so as to match the retention time obtained when the standard is injected into the target GC systems to the reference retention time. Finally, the standard may be injected again at the new head pressure to confirm that the retention times are locked. To ensure that the reference GC system remains locked during development of the mass spectral database, the column head pressure is periodically adjusted such that the retention time of the standard remains at the defined value.

Figure 3:
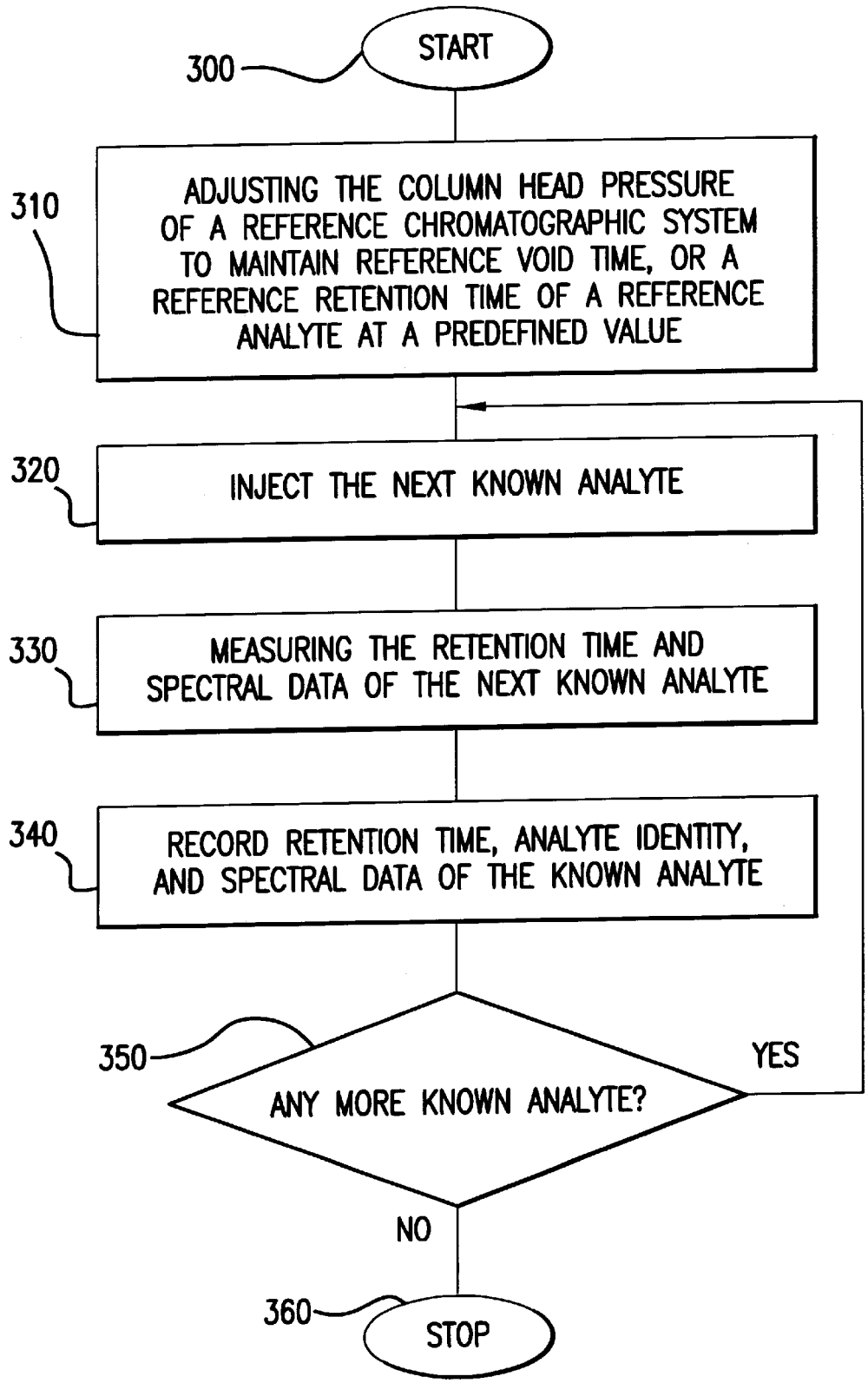
FIG. 3 is a flowchart illustrating the method steps for constructing a retention time-locked spectral database.

FIG. 3 illustrates a flowchart setting forth the method steps for constructing a database. At step 310, the column head pressure of a reference chromatographic system is adjusted to maintain the reference void time, or a reference retention time of a reference analyte at a predefined value. At step 320, a known analyte is injected and the retention time and spectral data of the known analyte is measured. At step 340 retention time, analyte identity, and spectral data of the known analyte are recorded. The data base is completed by stepping through the process until there are no additional analytes (step 350).

Figure 4:
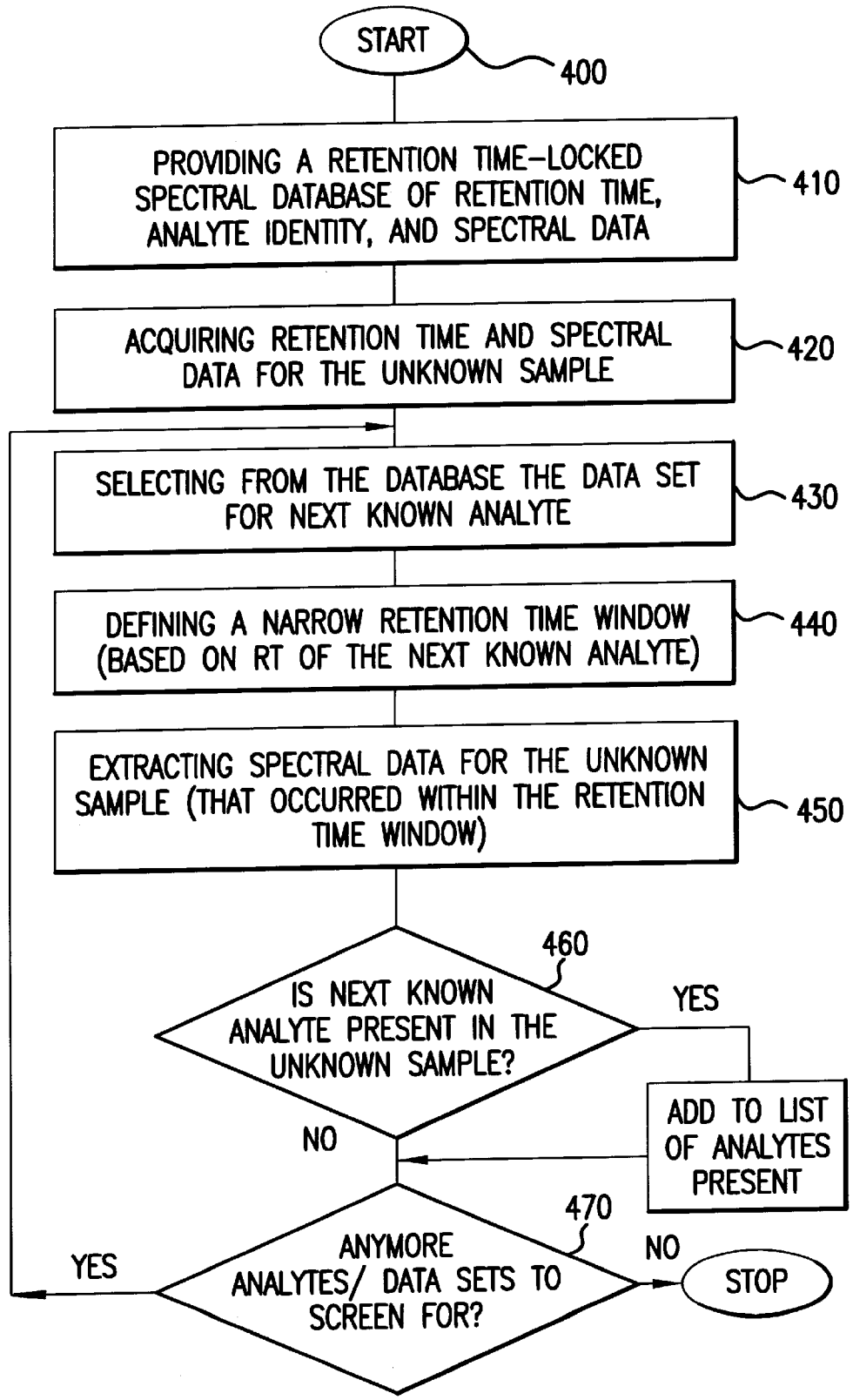
FIG. 4 is a flowchart illustrating the method steps for screening a retention time-locked spectral database.

FIG. 4 illustrates a flowchart of the method for identify known analytes in a known retention time (RT) locked database. Step 410 begins with the creation of the retention time-locked spectral database of retention time, analyte identity, and spectral data. In Step 420, the retention time and spectral data for the unknown sample is obtained. The data set for a known analyte is then selected from the database (430) and a narrow retention time window is defined (440) which is based on RT of the known analyte. At step 450, spectral data for the unknown sample is extracted within the retention time window. If the ions are present with the correct mass ion ratios, that compound is listed in the report as contained in the unknown sample. If the correct ions are present but the mass ion ratios are out of the preselected boundary, then the compound is listed in the report with a flag to indicate that the ion ratios are not matched (460). The system then steps down to the next analyte in the database and extracts its characteristic ions inside a window surrounding its locked retention time. The process is repeated until the chromatogram has been searched for every target analyte in the database 470.

Since the extraction is done only inside a narrow window around that compound's previously-determined locked retention time, the screening method is more specific and can be performed more rapidly than prior art methods.

Method translation may also be employed for converting the retention times in the retention time database to correspond to a locked GC system having different column and operating parameters than those employed for generating the retention time database such that analytes of interest can be accurately searched in the retention time database by retention time. Implementation of method translation is disclosed in commonly assigned U.S. Pat. No. 5,405,432, issued on Apr. 11, 1995 to Snyder et al. and hereby incorporated by reference.

The mass spectral information used for analyte identification and stored in the locked database with each compound can be generated using any reproducible mass spectral ionization technique. This would include (but is not limited to) EI (electron impact), PCI (positive chemical ionization) NCI (negative chemical ionization) and MS/MS techniques (including quadrupole, ion trap, magnetic sector, time of flight, etc.).

Furthermore, retention time-locked spectral database searching could be applied to a GC coupled with any kind of spectral detector. For example, the technique could be applied to GC with infrared detection (GC/IR) or atomic emission detection (GC/AED) techniques that are in common use today, as well as other spectral techniques that are not now commonly used for GC detection today. Any spectral feature or combination of spectral features that are characteristic of a molecule could be stored in a locked database. By locking the GC method to the database, the analyst could then search for these characteristic spectral features inside of a narrow retention time window around the locked retention time (or retention factor) of the analyte.

The invention may be automated so that chromatographer can step through an entire table of compounds, searching a chromatogram for the characteristic spectral features of each entry. For example, one could generate a spectral database of compounds consisting of their locked retention times (or retention factors) and infrared spectral characteristics. This locked method could then be repeated with unknown samples. After analysis, one could search the GC/IR chromatogram at the retention time of each entry in the database (inside a narrow RT window), looking for characteristic IR absorbance frequencies. If found, the compound would be recorded as present; if not found, the compound would not be recorded or would be recorded as absent.

As a filter to help determine if a compound is present at its locked retention time, one could use the presence or absence of characteristic spectral information and/or the ratio of characteristic spectral responses. For example, in GC/IR, one could simply look for the presence of characteristic absorbances at a compound's locked retention time. For more specificity, one could use the ratio of those characteristic absorbances. Any spectral characteristics could be used in this manner to determine if a target compound has eluted at its locked retention time. This could be (but is not limited to) mass ion ratios in GC/MS, absorbance ratios in GC/IR, the ratio of emission line intensities in GC/AED, the ratio of peaks at characteristic NMR frequencies (or chemical shifts), or the ratio of UV or visible light absorption at different wavelengths.

If data for target analytes are available from more than one spectral detector, these data could be combined in a single search. For example, both mass spectral and infrared data could be stored in a single retention time-locked spectral database. It would be possible to search two locked chromatograms (one GC/MS and one GC/IR) at each compound's locked retention time to determine if the correct mass and infrared spectral characteristics were simultaneously present. In principle, any amount of spectral data accumulated from one or more spectral detectors could be combined for use in this way.

The invention advantageously incorporates retention time locking to ensure the repeatability of retention times (or retention factors) for a given method, from run to run, on a single instrument or between different instruments. Improved retention time precision provides for the creation of useful databases of target analyte retention times. Along with the locked retention times, one can incorporate spectral characteristics for each analyte in the database. When analyzing unknown compounds, the analyst locks his or her method to the database so that all analyte retention times (or retention factors) closely match the database values. After analysis, one can search the chromatogram (or even multiple chromatograms, so long as they are all locked to the database) for every compound listed in the database, using both retention time and its spectral features for identification. Retention time locking enables one to search for a compound's spectral features inside a narrow retention time window drawn around the analyte's locked retention time.

While the invention has been described and illustrated with reference to specific embodiments employing retention time locking in combination with mass spectrometry type detectors, those skilled in the art will recognize that the invention works equally well for other types of spectral detectors, such as infrared detection, that can be employed in combination with the invention to assist in identifying unknown analytes having retention times ascertained under locked conditions.

What is claimed is:

1. A method for screening an unknown sample for a plurality of known analytes with a gas chromatograph (GC) operated at a programmed column head pressure, comprising the method steps of:

providing a retention time-locked spectral database comprising a plurality of data sets, each data set having retention time, analyte identity, and spectral data for a corresponding one of the plurality of known analytes in said plurality of know analytes;

acquiring retention time (RT) data and spectral data for the unknown sample;

selecting from the database the data set for a first known analyte;

defining a narrow retention time window around the retention time of the first known analyte;

extracting spectral data for the unknown sample that occurred within the retention time window, and comparing it with the spectral data for the first known analyte to determine whether the first known analyte is present in the unknown sample; and repeating the steps of selecting, defining, extracting, and comparing for each known analyte in the spectral database so as to screen the unknown sample for all known analytes.

2. The method for screening an unknown sample for a plurality of known analytes as claimed in claim 1, wherein the method step of providing a retention time-locked spectral database further comprises the method steps of:

adjusting the column head pressure of a reference chromatographic system such that a reference void time, or a reference retention time of a reference analyte, is maintained at a predefined value;

injecting the first known analyte into the reference gas chromatographic system;

measuring the retention time and spectral data of the first known analyte;

recording the retention time, analyte identity, and spectral data of the known analyte in a first data set of the spectral database; and repeating the steps of injecting, measuring, and recording for each known analyte so as to construct each data set of the spectral database under retention time locked operating conditions.

3. The method for screening an unknown sample for a plurality of known analytes as claimed in claim 2, wherein the method step of acquiring retention time and spectral data for the unknown sample further comprises the method steps of:

retention time-locking a target GC chromatographic system to the reference chromatographic system by adjusting the column head pressure of the target GC chromatographic system such that the measured void time is matched with the reference void time, or the measured retention time of the reference analyte is matched with the reference retention time of the reference analyte.

4. The method for screening an unknown sample for a plurality of known analytes as claimed in claim 3, wherein the method step of acquiring retention time and spectral data for the unknown sample further comprises the method steps of periodically adjusting the column head pressure such that the retention time remains at the defined value to ensure that the reference GC system remains locked during development of the mass spectral database.

5. The method for screening an unknown sample for a plurality of known analytes as claimed in claim 1, the step of acquiring retention time and spectral data for the unknown sample further comprising acquiring mass spectral ions and mass spectral ion ratios of the unknown sample.

6. The method for screening an unknown sample for a plurality of known analytes as claimed in claim 5, further comprising the step of generating a report listing the characteristic ions present with the correct mass ion ratios, and if the correct ions are present but the mass ion ratios are out of the preselected retention time boundary, then the compound is listed in the report with a flag to indicate that the ion ratios are off.

7. The method for screening an unknown sample for a plurality of known analytes as claimed in claim 1, the step of selecting further comprising stepping down to the next analyte in the database and extracting its characteristic ions inside a retention time window surrounding its locked retention time.

8. The method for screening an unknown sample for a plurality of known analytes as claimed in claim 3, further comprising the step of translating a chromatographic method for the target chromatographic system such that retention times in the spectral database correspond to those obtained on the target chromatographic system having different column and operating parameters than those employed on the reference chromatographic system used for generating the retention time-locked spectral database.

9. The method for screening an unknown sample for a plurality of known analytes as claimed in claim 5, wherein the mass spectral ions and ratios used for analyte identification and stored in the database is generated using any reproducible mass spectral ionization technique, including EI (electron impact), PCI (positive chemical ionization), NCI (negative chemical ionization) and MS/MS (mass spectrometry).

10. The method for screening an unknown sample for a plurality of known analytes as claimed in claim 1, further comprising a gas chromatograph (GC) coupled with any kind of spectral detector, including infrared detection (GC/IR), or atomic emission detection (GC/AED) techniques.

11. The method for screening an unknown sample for a plurality of known analytes as claimed in claim 1, further comprising detecting for infrared spectral characteristics using infrared detection, generating a GC/IR chromatogram at the retention time of each entry in the database (inside a narrow RT window), and searching characteristic IR absorbance frequencies.

12. The method for screening an unknown sample for a plurality of known analytes as claimed in claim 11, wherein the presence or absence of characteristic spectral information and/or the ratio of characteristic spectral responses at a compound's locked retention time is used to determine if an analyte has eluted at its locked retention time.

13. The method for screening an unknown sample for a plurality of known analytes as claimed in claim 1, further comprising the step of acquiring retention time and spectral data for the unknown sample from a plurality of spectral detectors, wherein two locked chromatograms at each analytes locked retention time are searched to determine if the associated spectral characteristics were simultaneously present.

14. The method for screening an unknown sample for a plurality of known analytes as claimed in claim 13, wherein the plurality of spectral detectors further comprises a mass spectral detector and an infrared detector such that both mass spectral data and infrared data could be stored in a single retention time-locked spectral database, and wherein two locked chromatograms (one GC/MS and one GC/IR) at each analytes locked retention time are searched to determine if the correct mass and infrared spectral characteristics were simultaneously present.

* * * * *

UNITED STATES PATENT AND TRADEMARK OFFICE
CERTIFICATE OF CORRECTION

PATENT NO. : 5,939,612
DATED : 08/17/99
INVENTOR(S) : Philip L. Wylie et al.

It is certified that error appears in the above-indentified patent and that said Letters Patent is hereby corrected as shown below:

Claim 4, line 6, "the retention time" should read -- the reference retention time --

Signed and Sealed this

Eighteenth Day of January, 2000

Attest:

Q. TODD DICKINSON

Attesting Officer

Commissioner of Patents and Trademarks